United States Patent [19]

Chevalier, Jr. et al.

[11] Patent Number: 5,401,257
[45] Date of Patent: Mar. 28, 1995

[54] URETERAL STENTS, DRAINAGE TUBES AND THE LIKE

[75] Inventors: Raymond P. Chevalier, Jr., Bloomington, Ind.; Christopher J. Ernster, Charlestown, Mass.

[73] Assignee: Boston Scientific Corporation, Watertown, Mass.

[21] Appl. No.: 53,163

[22] Filed: Apr. 27, 1993

[51] Int. Cl.⁶ ............................................. A61M 5/00
[52] U.S. Cl. ................................. 604/265; 606/195; 604/93; 604/280
[58] Field of Search ........................ 604/52-53, 604/171-172, 264-266, 270, 93, 109, 280; 606/195

[56] References Cited

U.S. PATENT DOCUMENTS

| | | | |
|---|---|---|---|
| 1,920,006 | 7/1933 | Dozier . | |
| 3,780,740 | 12/1973 | Rhea | 128/350 |
| 4,212,304 | 7/1980 | Finney | 604/93 |
| 4,307,723 | 12/1981 | Finney | 128/349 |
| 4,610,657 | 9/1986 | Densow | 604/8 |
| 4,692,152 | 9/1987 | Emde | 604/164 |
| 4,698,056 | 10/1987 | Ciannella | 604/164 |
| 4,790,310 | 12/1988 | Ginsburg et al. | 128/303 |
| 4,827,940 | 5/1989 | Mayer et al. | 128/642 |
| 4,876,126 | 10/1989 | Takemura et al. | 604/265 |
| 4,936,835 | 6/1990 | Haaga | 604/265 |
| 5,049,138 | 9/1991 | Chevalier et al. | 604/265 |
| 5,120,317 | 6/1992 | Lutner | 604/164 |
| 5,205,830 | 4/1993 | Dassa et al. | 604/164 |

OTHER PUBLICATIONS

Microvasive brochure, FADERtip TM Dissolving Tip Ureteral Stent.

Primary Examiner—C. Fred Rosenbaum
Assistant Examiner—Chalin Smith
Attorney, Agent, or Firm—Fish & Richardson

[57] ABSTRACT

A ureteral stent of a small tubular size, e.g., 6 French, with an enlarged entry end of the stent tube, a dissolving tip of satisfactory strength and dimension that can be secured in the tube and a bore that can be incorporated in the tip enabling passage of an 0.038 inch guidewire having the desired stiffness characteristics. Stents according to the invention incorporate a tip of sufficiently large size that the tip can be reliably manufactured and secured to the stent body. The invention also includes medical devices with informational markings formed by application of laser radiation.

10 Claims, 1 Drawing Sheet

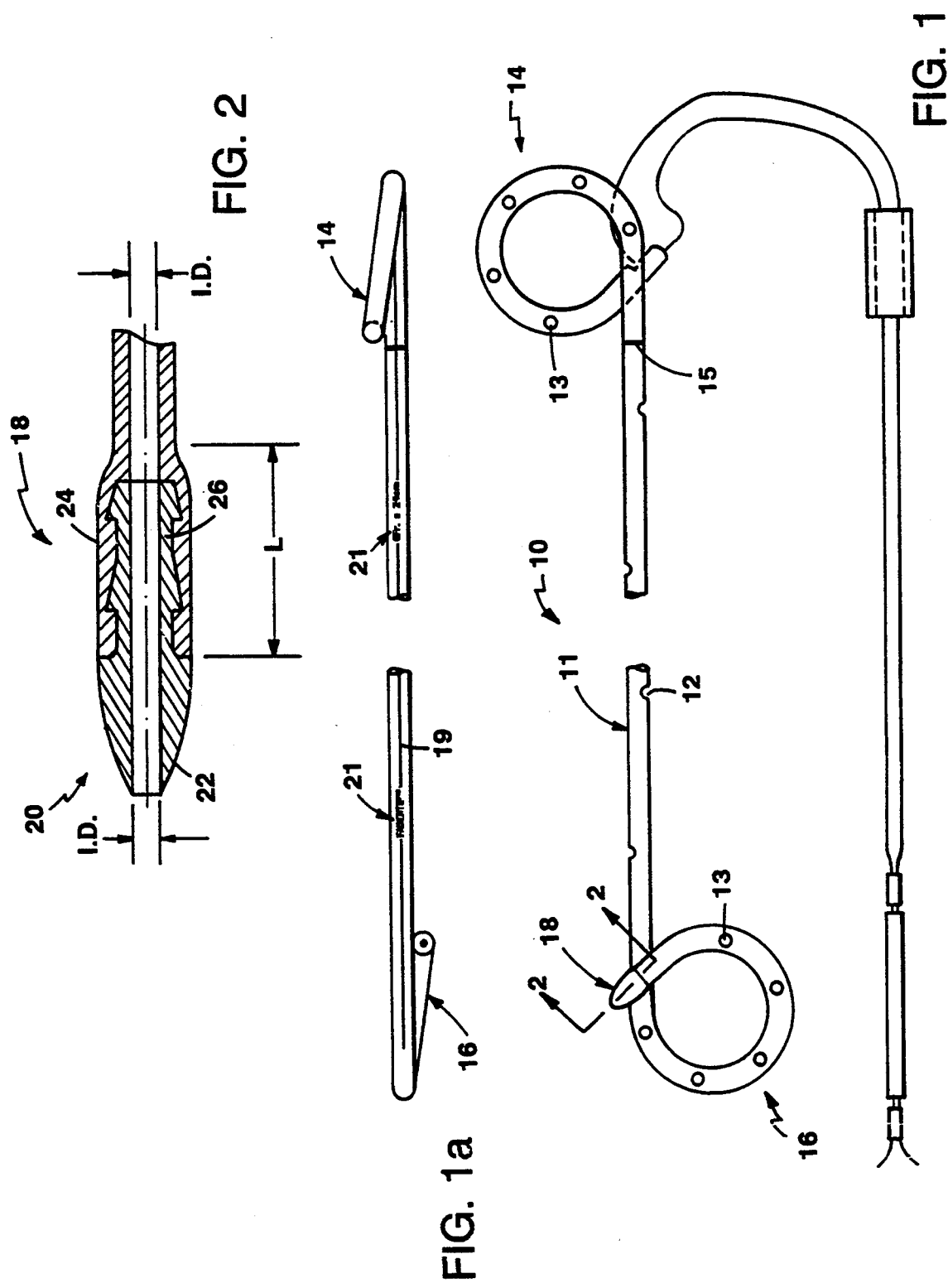

URETERAL STENTS, DRAINAGE TUBES AND THE LIKE

FIELD OF THE INVENTION

This invention relates to ureteral drainage stents. It also has potential application to other cases where it may be important to simultaneously realize small catheter size, special end tip characteristics and ability to pass over a relatively large guidewire. The invention also relates to marking medical articles.

BACKGROUND OF THE INVENTION

When a patient has an obstruction of the ureter, it is common to relieve the obstruction with a ureteral stent to enable urine to pass from the kidney to the bladder. Typically, the stent extends from the kidney to the bladder. In some cases, the stent has a retention configuration, such as a pigtail, at its ends in the kidney and the bladder.

A common case of ureteral obstruction is the ureteral stone, while cancerous tumor or a feature of the anatomy that allows ureter kinking can also produce ureteral obstruction.

Another occasion for use of a ureteral stent is after lithotripsy has been performed to break up a stone. A stent may be placed to allow fragments of stone to pass from the body and enable the ureter to heal.

Ureteral stents may be introduced to the body either percutaneously in an antigrade fashion, using, for example, an adaptation of the Seldinger technique, or cystoscopically in a retrograde fashion. The stents positioned in the bladder through a cystoscope are passed into the ureter using direct vision through the endoscope positioned in the bladder. For thus placing the stent there are two common methods. One is the so-called over-the-wire placement method. A guidewire of sufficient stiffness and maneuverability is inserted into the ureter under endoscopic guidance. When access past the ureteral obstruction to the kidney is achieved, the stent is introduced to the ureter over the wire by a pusher catheter acting on the trailing end of the stent. The common guidewire size that urologists prefer is 0.038 inch diameter, selected to be stiff enough to negotiate past the obstruction, but small enough to enable passage of a small stent over it.

The second common endoscopic placement method for ureteral stents, which omits the prior step of placing a guidewire, may be used where no large obstruction is indicated. In this method, the guidewire is inserted through the stent only until it is flush with or within the tip of the stent. A pusher is again inserted behind the stent on the guidewire and is locked to the guidewire with a locking hub (e.g. Speed-Lok ® product available from Boston Scientific Corporation, Watertown, Mass.). The assembly is then pushed by the pusher catheter acting on the trailing end to enter the cystoscope and then the ureter.

The choice of technique is based on physician preference and evaluation of the patient. For instance, if the obstruction is small, the physician may first try to use the retrograde technique in which the wire does not extend beyond the entry end of the stent for saving time and cost. But if that technique is unsuccessful, the stent is withdrawn and the guidewire is inserted retrograde. As the wire is much smaller in diameter than the stent it can more easily be negotiated past the obstruction. When the wire is successfully placed, the stent is passed over the wire. The over-the-wire technique is usually more reliable and less traumatic to the patient, and also may lessen the risk of ureteral perforation or puncture.

It is preferable for the hospital to be able to stock one stent unit to be used in both retrograde placement techniques as it involves less inventory cost. Also a dual-use stent allows the physician to have both options when he opens the package. It is therefore highly desirable that a single stent be capable of both types of placement and capable of using a guidewire as large as the common 0.038 inch guidewire.

It is likewise desirable for a stent to carry markings of its identity so that, for instance, a physician, when withdrawing a used stent, can determine e.g. its length, French size and style, to be able to assuredly select a replacement stent of identical character.

Furthermore, it has been found that by using a hydrophilic, dissolving tip on the end of a ureteral stent, significant advantages can be obtained, as are disclosed in U.S. Pat. No. 5,049,138, which is hereby incorporated by reference. In this case two very dissimilar materials are employed with two different desirable attributes. The dissolvable tip is very rigid and hydrophilic (lubricious) which both assist in non-traumatic placement. The body of the catheter to reside in the ureter is very soft and pliable for patient comfort and for avoidance of trauma over the duration of its residence in the ureter. By being dissolvable, the hydrophilic entry tip disappears after it has been useful in the placement of the softer material in the ureter. The dissolution of the tip provides a larger passage for improved drainage.

In respect of long-term patient comfort, peristaltic action of the ureter constantly occurs, in normal function. This produces forces and sensations associated with attempted expulsion of the stent. To diminish these tendencies and improve patient tolerance, it is highly desireable that the stent be as small in diameter as will perform the drainage task. Also, the smaller the stent, the easier it is to pass through the endoscope and pass the ureteral obstruction.

Heretofore, however, it has not been possible to put a dissolving or hydrophilic tip on a stent of the desired small 6 French size, while having the capability to place the stent over the widely preferred wire size of 0.038 inch diameter. Such combination has appeared unachievable because of the dimensional characteristics and requirements of the components.

SUMMARY OF THE INVENTION

It has been realized that, in contexts where small size of endwise-insertable tubular catheters or stents may be deemed of critical importance, that nevertheless using a slightly enlarged entry tip can provide a substantial overall benefit, by enabling use of a separately fabricated entry tip member, the enlarged size accommodating sleeve-type interconnection between the parts, the entry tip member providing desirable entry qualities such as relative rigidity, hardness, or low friction surface in the tip region, or other qualities such as dissolvability; on balance such desirable entry quality or qualities are found capable of off-setting any undesirable effect of the enlarged entry size, and provide an over-all improved tubular catheter or stent.

It has been discovered that by making a ureteral stent of a small tubular size, e.g., 6 French, but enlarging the entry end of the stent tube, a dissolving tip of satisfactory strength and dimension can be secured in the tube and a bore can be incorporated in the tip enabling passage of an 0.038 inch guidewire having the desired stiffness characteristics.

Stents according to the invention incorporate a tip of sufficiently large size that the tip can be reliably manufactured and secured to the stent body.

In preferred embodiments, the dissolvable tip is polyvinyl alcohol containing glycerin as a plasticizer. Such a material is high in viscosity and very difficult to mold. The present invention enables meeting the wall thickness constraints for moldability and strength while accommodating a through-hole that enables passage of the 0.038 inch wire. In this way a sufficient tubular wall thickness in the connection region, e.g., 0.008 or 0.010 inch, can be achieved to enable the entry tip member to be reliably molded and secured in a pre-enlarged end of a 6 French catheter of conventional soft material.

In preferred embodiments the stent is constructed by forming an enlarged end on a soft stent tube, inserting a connector shank of the separately formed tip member, and forming the tube material about the shank. Preferably thermo-forming of the tube material is employed for both preforming and post-insertion tasks.

While the invention has been occasioned by the need for an improved small diameter (e.g. 6 French), over-the-conventional-wire (e.g. 0.038 inch) ureteral stent having a dissolvable tip, it is realized that the present invention has broader potential applicability for realizing two part stents and catheter constructions having severe size constraints in which the entry tip can provide desirable properties different from the main body of the stent or tube.

BRIEF DESCRIPTION OF THE DRAWING

FIG. 1 is a view of the preferred ureteral stent according to the invention;

FIG. 1a is another view of the stent (rotated 90° out of the page) in FIG. 1; and FIG. 2 is an enlarged longitudinal cross-section taken on line 2—2 of FIG. 1.

DESCRIPTION OF THE PREFERRED EMBODIMENT

In the preferred embodiment, the stent 10 is a tubular member of selected thermo-plastic polymer selected for suitable flexibility. Examples are low molecular weight urethane, the material C-Flex TM available from Concept Polymers of Clearwater Florida and Percuflex TM stents available from Boston Scientific Corporation. The main body 11 of the stent is of 6 French outer diameter consistently throughout its length, except for a short tip portion 18 at the kidney "pigtail" retention formation. The tip portion of the stent, about 1 cm length, is enlarged to approximately 7.5 French. The tip formation is formed partly by bullet-shaped leading tip 22 of hydrophilic, dissolvable tip member 20 and partly by the enlarged portion 24 of the stent tube that lies over and securely engages the barbed connector shank portion 26 of the tip member. The tip member is on the distal end of the stent which is introduced first into the body.

In the preferred embodiment, the stent has ends shaped by thermal methods into Circular pigtail retention formations 14 and 16 and is between 10 to 30 cm in length between the pigtail formations, depending upon patient size. It has drainage holes 12 throughout its length.

The drainage holes are spaced approximately 1.5 cm apart over the length of the main body 11 of the stent, these lying in a spiral pattern down the length of the body. On the pigtail retention formations, the holes are spaced 1.5 cm, in line. The stent has a placement marking 15 at its bladder pigtail end that is used for visualization by the physician to know when the appropriate length of stent has been inserted into the ureter. Referring to FIG. 1a, the stent also includes a medial line 19 down the spine of the stent, which is used to orient the pigtails. These and other markings 21, e.g. size and manufacturer, may be made by laser scribing techniques, which are discussed in more detail below. The dissolving tip placed in the kidney pigtail end of the stent is made of a thermo-plastic material, e.g., polyvinyl alcohol plasticized with glycerin, formed by injection molding, see the above referenced patent for details.

In manufacture, the end of the 6 French tubing is preformed to accept the tip member by heating a teflon mandrel and pushing it the required distance into the end of the tube, thereby causing the polymer of the tubing to flow and stretch to a larger size in this localized tube region. The tube is then allowed to cool and the mandrel is removed, with the tube end holding its enlarged diameter. The shank 26 of the tip member 20 is then inserted with an interference fit into the end of the tubing, while a 0.041 inch diameter wire mandrel is maintained in the bore of the affected region, i.e. in the tip of the stent lumen and the tip member. The united region of the tip member and the stent are then inserted into a heated mold to displace the thermo-plastic material of the stent body into tighter engagement around the barbs of the tip member. The part is then cooled, and removed from the mold and the wire mandrel is removed from the stent, allowing the preformed pigtail to reform to its preset shape. The length of the enlarged region of the stent tubular body 11 is approximately 5 millimeters.

In more detail, the final molding procedure is accomplished with a mold formed by an aluminum block in which a hole has been drilled, sized appropriately for the outer final diameter of the enlarged tip portion. That mold has a tapered lead-in to facilitate placement of the tipped stent assembly into the mold. The mold is heated with RF energy or other means of heating. The assembled catheter is pushed through this heated mold bore. Passage end-on through the bore displaces the thermo-plastic material of the stent body and smooths it out over the length of the retention barbs. The effective zone of the mold matches in length the transition zone of the barbs a distance of approximately 5 millimeters. Because the material flow during this molding step is in the inverse direction toward the bladder end of the stent, the extra material is compressed and formed intimately around the barbs and around the back of the tip member with no detrimental mold flash or interruption to the smoothness of the entry end of the stent.

By having the 0.041 mandrel in place during this post connection operation, the lumen opening is maintained straight and of design diameter in both of the joined parts.

The melt temperature of the dissolvable material is much higher than the melt temperature of the very soft thermo-plastic that is preferred, so that its contour is not affected by this heat-molding operation.

After this step no further finishing operation is required. After the end assembly cools, it is removed from the mold, the mandrel is removed and the pigtails are allowed to return to their pre-set shape.

In use, this product facilitates placement into the body over an 0.038 inch diameter guidewire as well as by using techniques in which the guidewire does not extend beyond the entry end of the stent. By using the invention it has become possible to incorporate a tip of dissolving material with its desirable rigid and hydrophilic features for ease of placement and tractability past a tortuous obstruction, while in addition enhancing patient comfort by leaving a small stent in place. During placement, because of its hydrophilic nature, and associated lubricity in the presence of urine, the tip is found to slide smoothly through the ureter without causing trauma, despite its enlarged size. Still the main body of the stent, as mentioned, is of the preferred small size, 6 French, of very soft, patient-comfortable material.

In the case of over-the-wire retrograde placement of the stent over the 0.038 inch wire guide, in the usual way the wire is put up through the ureter, past the obstruction, and then the stent is passed over the wire and pushed from its trailing end past the obstruction with a rigid push catheter or piece of tubing. The rigid and hydrophilic tip tracks nicely over the guidewire. Once the stent is in place, the wire is removed and the pigtails are allowed to reform in both the kidney and the bladder to retain the stent in place for its useful life. The dissolving mechanism of the tip material is strongly activated within minutes after placement and totally dissolves within two hours, just prior to the anesthesia from the procedure wearing off. By the time the anesthesia wears off only a very soft biocompatible polymer tube of the appropriate small size for comfort is left in place, and remains there during the time required. In addition, the stent retains an enlarged entry region in the place where the dissolving tip material previously resided. This enlarged entry can facilitate entry of stone fragments or debris that may be left from the procedure to assist in their capture and excretion. The enlarged end also will facilitate greater flow during the useful life of the stent. The relatively large diameter of the tube end is of no detriment to the patient because it lies within the confines of the retention pigtail, in the renal pelvis of the kidney that accommodates such size.

In the second preferred retrograde placement technique the guidewire is placed through the lumen of the catheter and aligned flush with the bullet shaped dissolving tip, to act as a stiffener or straightener to straighten the stent in the usual way. The pusher is then placed behind the stent and locked to the wire (Speed-Lok ®, Boston Scientific Corporation, Watertown, Mass.). The locked assembly is then passed up the ureter as a complete unit. When pushing the stent in this method, all of the attributes of the lubricious, dissolving tip still apply in facilitating entry using the preferred wire size. Once the stent is in place, the same thing has been accomplished as before, i.e., the placement of a small preferred diameter tubing that is very soft and provides patient comfort for its long-term use.

It has been noted above that during passage of the relatively large end of the stent in either placement technique, the patient is under anesthesia and has no sensation. In fact, this tip is believed to be less traumatic than the 6 French end of a conventional stent because the dissolvable material of the tip is hydrophilic and slippery in the presence of body fluids, and is hence less likely to cause friction damage to the soft and vulnerable ureteral tissue. It is noted that the primary ureteral injury that can occur, ureteral inflammation, is caused by friction and irritation caused by sliding a stent through the ureter. Because of its high lubricity, less frictional damage occurs. The somewhat increased localized side pressure related to the somewhat enlarged local end diameter can be accommodated by temporary stretching of the diameter of the ureter without damage.

Furthermore, a primary advantage of this invention is the enablement of placement over the physician-preferred wire size to reduce the risk of ureteral perforation. For instance, when being pushed past an obstruction, in the absence of a wire, the stent tends to veer off course and the soft spongy ureteral tissue can be punctured easily. By use of the guidewire, the present device will track more accurately around the obstruction and through the ureter without such risk of perforation. Indeed even if use of this product were restricted to the over-the-wire mode of introduction, it would have the virtues of the hydrophilic nature of the tip and the attendant ease of placement while achieving a small size of soft stent material, with eventual disappearance of the tip to enhance drainage capability.

In regard to a preferred specific embodiment it is preferable that the nominal bore of the tube and the tip member be the same, of the order of about 0.044 inch for passing an 0.038 inch wire. To facilitate placement over that wire one needs such a degree of clearance between the wire and the actual stent itself. In manufacture, the two mating parts will achieve an 0.044 inch dimension in the large majority of cases. The tolerance direction for the preferred 0.004 inch tolerance for the bore of the tip member is in the smaller direction to ensure good trackablility of the tip member on the wire and to ensure that the wall thickness of the shank is sufficient for manufacturability (mold filling) and strength. Because of its hydrophilic nature a close-fitting tip member will not drag excessively on the wire, i.e. not as much as a hydrophobic material might. Also, since the length of such close tolerance extends approximately only one centimeter, much less than the total length of the product itself, little drag is experienced due to closer fitting of the tip.

In the preferred embodiment, the tolerances for the 0.004 inch internal diameter of the stent shaft itself is chosen in the direction of a larger bore. If slight variation does occur, it will enhance the drainage capability of the stent and limit the risk of guidewire friction that may be achieved in passing the stent over the guidewire, which can have an overall length as long as 35 to 45 cm.

Numerous alternative methods can be employed for forming the end of the stent tube, for receiving the tip member.

For instance, a mechanical stretching of the tube can be employed and then relaxation of the tube over the tip without use of heat. Also technical extrusion processes can be employed to provide the preformed enlarged end shape to the tube. For instance during extrusion of the tube, drawing or stretching and then periodically relaxing for a short distance and then stretching again can be employed. The diameter will be larger at the points of relaxation. The tube can be cut at these points so that diameter is expanded at that end.

Referring further to the figures a monofilament suture 40 is attached to the most proximal end of the bladder coil and to the other end of that suture a piece of tubing is crimped, which the physician can hold as a handle. This is useful if the physician inadvertently passes the stent too far up the ureter and needs to pull it down or remove it because of complication in the case. The additional piece of tubing shown half way down the suture is an attachment collar that is attached to hold the suture parallel to prevent tangling prior to use. When the product is removed from the package, the plastic collar is removed and discarded.

As noted above, the stent that has been described is constructed to enable passing through the working channel of an endoscope. The endoscope enables the doctor to visualize the stent and its placement. Although rigid endoscopes are commonly employed for stent placement, increasingly in practice, smaller scopes with smaller working channels are preferred because they can be passed further up the ureter for diagnosis. The ability to employ a smaller stent assists in the choice of a smaller endoscope with smaller working channel. The lubricity and relative short length of the relatively large tip member of the present catheter helps it pass through the relatively small channel.

The stent may be part of a kit, which also includes the positioning or pushing catheter, and a guidewire, preferably of 0.038 inch diameter. Wires of varying stiffness, from rather flexible to super stiff, may be used. For example, a 0.038 inch, stiff wire with a 3 cm flexible tip may be provided. The wire may be a 0.038 inch Glidewire ® (Boston Scientific Corporation, Watertown, Mass.), which is hydrophilically coated. The wire may be a 0.038 inch Lubrigide ® wire (Boston Scientific Corporation, Watertown, Mass.), a stainless steel wire with 3 cm flexible tip and also including a hydrophilic coating. A 5 French ureteral catheter may also be included as part of the kit. The ureteral catheter is a straight piece of tubing 70 cm long, having inch graduations every centimeter to 50 cm and an adjustable luer-lock hub. The catheter is used by the doctor to evaluate and access the ureter prior to stent placement. The wire is placed in the ureter, followed by the ureteral catheter, which is used to diagnose the tract by injecting contrast materials that indicate the location of obstruction.

(We note that in certain circumstances the entry end of a ureteral catheter may likewise be provided with a separately fabricated, entry-facilitating end tip member of slightly enlarged outer diameter to facilitate the connection, in general manner as described above.)

In some embodiments, the stent can be used with smaller, e.g. 0.025 inch, guidewires, which may be used to position an endoscope which accepts a laser fiber in one working channel and the guidewire in the other working channel. After application of laser energy, the laser and endoscope are removed from the body over the guidewire, leaving the guidewire in the body. The stent can then be positioned over the 0.025 guidewire in a manner similar to that discussed above.

As indicated above, the stent includes markings, such as marking 15 for locating the stent within the ureter and marking 19 down the spine of the stent, which is used to orient the pigtail in the desired direction. These markings, as well as others that indicate the size, length and manufacturer of the stent, can be placed on the stent using a laser scribing system. The system (Model 1750 Universal Laser Systems, Scottsdale, Ariz.) includes a ND-Yag (50 watt, pulse rate 39,949 per cm, pulse width 10 microseconds, pen speed 9 cm/sec) laser and a plotter-positioner that locates the laser energy in accordance with a computer program that may be downloaded from, for example, a CAD system, e.g. Autocad ® drafting system. The tubing to be used in the stent, prior to forming retention curls or drainage openings, is placed on the plotter unit using positioning grooves and a mandrel that keeps the tube straight. The laser scribing unit is then driven by the program to laser-write the desired pattern on the tubing. The tubing is then removed from the system and cleaned with a non-reactive solvent (e.g. freon or alcohol) to remove loose residue. In a particular embodiment, the tube (wall thickness 0.015–0.030 inch) is formed of Percuflex polymer (ethylvinyl acetate (EVA)), with a radiopacity enhancing additive, preferably bismuth subcarbonate (30% by weight). In another embodiment, the polymer is C-flex TM, which includes bismuth oxychloride (30% by weight) and colorants as additives (Concept Polymers, Clearwater, Fla.). The markings are visible because they are of a different color, usually dark charred color, than the tube material. The markings are also relieved into the surface of the tube. The marked tube is free of toxic byproducts and compatible for use within the body.

While the laser burns, oxidizes or otherwise removes the tubing polymer, in some cases, additives within the polymer matrix enhance the marking effect. For example, PVA without additive is clear and is not effectively marked by the laser, while EVA with the above noted radiopacity enhancing additive is white and is found to be effectively marked by the laser described above. Other laser and polymer combinations may be used with other selected additives to enhance the marking effect. For example, C-flex with the oxychloride additive noted above can also be marked with a $CO_2$ laser.

Marking the stent in this manner is particularly useful since introduction of another material, such as an ink, is avoided. Further, the markings are retained even after the stent has been within the body for an extended period of time, for example the maximum useful life of typically six to eight weeks. On removal of the stent, the doctor can easily determine the size and length of the stent, and its manufacturer, for selecting and restenting the patient, without remeasuring the length of the ureter by fluoroscopy.

These and other embodiments can be constructed within the spirit and scope of the following claims.

What is claimed is:

1. In a ureteral stent or the like comprising a main catheter body of flexible material having an internal bore of diameter closely corresponding to the outer diameter of a predetermined guidewire with which said main catheter body is constructed to be used, the internal surface of said main catheter body being exposed to directly engage said guidewire, and a tip member at the distal end of said main catheter body, said tip member comprised of hydrophilic material that readily dissolves when contacted with body fluids to which said stent is intended to be exposed and having a through-bore substantially corresponding to the through-bore of said main catheter body, said tip member having two portions, an end portion constructed to serve as the distal end of said stent and an integral connector shank portion smaller in outer diameter than said end portion and constructed to be securely engaged within a distal end portion of the main catheter body, the improvement characterized in that said distal end portion of said main catheter body is larger in outer diameter than the general outer diameter of the main catheter body, said distal end portion of said main catheter body being disposed about and secured to the exterior of said connector shank portion of said tip member, said construction enabling said main catheter body to be of relatively small outer diameter and of thin wall while securely holding said tip member, and, when said tip member is dissolved, providing an enlarged entry to said main catheter body for facilitating entry of fluid and debris.

2. The ureteral stent or the like of claim 1 formed of a radiation-sensitive polymeric material that has been selectively exposed to radiation to produce informational markings.

3. The ureteral stent or the like of claim 1 in the form of a tube constructed to be inserted endwise into a restricted body lumen in which a surface of said end portion is comprised of material that in use has low frictional resistance to sliding.

4. The ureteral stent or the like of claim 1 in which said hydrophilic material comprises polyvinyl alcohol and glycerine.

5. The ureteral stent or the like of claim 1 in the form of a tube constructed to be inserted endwise into a restricted body lumen and the end portion of said tip member is comprised of material more rigid than the material of said main catheter body.

6. The ureteral stent or the like of claim 1 wherein said tip member is sized to enable passage of a guidewire of outer diameter up to and including 0.038 inch.

7. The ureteral stent or the like of claim 1, wherein the tube is of thermo-plastic material and the distal end portion of said main catheter body is thermo-formed about retention formations on said connector shank.

8. The ureteral stent or the like of claim 1 in the form of a perforated drainage catheter.

9. The ureteral stent or the like of claim 1 in the form of a ureteral stent having retention formations for engagement in the bladder and kidney and a length matching the ureteral distance between those organs.

10. The article of claim 2 wherein said polymer includes an additive that enhances marking on exposure to radiation.

* * * * *